United States Patent [19]

Nakai et al.

[11] Patent Number: 4,902,622
[45] Date of Patent: Feb. 20, 1990

[54] NOVEL α-1,6-GLUCOSIDASE AND PROCESS FOR PRODUCING THE SAME

[75] Inventors: Kuniharu Nakai, Chita; Masayoshi Shiozaki, Nagoya; Hiroji Tsuji; Shigeharu Mori, both of Nishiharu; Susumu Hirose, Kakamigahara; Nobumasa Yokoi; Takaichi Ohya, both of Nishiharu, all of Japan

[73] Assignee: Amano Pharmaceutical Co., Ltd., Aichi, Japan

[21] Appl. No.: 100,730

[22] Filed: Sep. 25, 1987

[30] Foreign Application Priority Data

Sep. 26, 1986 [JP]  Japan ................................. 61-228904
Mar. 11, 1987 [JP]  Japan ................................. 62-56149

[51] Int. Cl.$^4$ ............................................. C12N 9/44
[52] U.S. Cl. ................................. 435/210; 435/252.2; 435/832
[58] Field of Search ....................... 435/210, 252.2, 832

[56] References Cited

U.S. PATENT DOCUMENTS 4,011,139  3/1977  Horwath et al. .................... 435/210

Primary Examiner—Robert A. Wax
Attorney, Agent, or Firm—Wegner & Bretschneider

[57] ABSTRACT

A novel α-1,6-glucosidase having the following properties:

(1) Action: The enzyme acts on an α-1,6-glucoside bond to produce linear amylose;

(2) Substrate specificity: The enzyme has the following relative activity to polysaccharides:

| Polysaccharide | Relative activity (%) |
|---|---|
| Pullulan | 100 |
| Maize soluble amylopectin | 13.5 |
| Soluble starch | 6.7 |
| Oyster glycogen | 1.7 |
| Hare glycogen | 2.6 |
| Maize amylopectin | 3.8 |
| Potato amylopectin | 4.0 |

(3) Km value and Vmax to pullulan: the enzyme has Km value of 0.14 mg/ml and Vmax of 70.0 μmol/min/mg protein;
(4) Optimum pH: 5.0 to 5.5;
(5) pH stability: The enzyme is stable in the pH range of 4.5 to 6.5 for 30 minutes at 40° C. and in the pH range of 5.0 to 6.0 for 30 minutes at 50° C.;
(6) Optimum temperature: Approximately 55° C.;
(7) Thermal stability: Treatment at pH 4.5 for 30 minutes at different temperatures indicates that the enzyme retained 80% of the initial activity at 40° C. and 10% thereof at 60° C.;
(8) Influence of inhibitor: The enzyme is inhibited by at least 70% by p-chloro-mercuribenzoic acid or sodium dodecylsulfate, but is not inhibited by o-phenanthroline or potassium ferricyanide;
(9) Influence of metal salts: The enzyme is negligibly affected by $Ni^{2+}$, $Ba^{2+}$, $Zn^{2+}$, $Cd^{2+}$ or $Mn^{2+}$; is inhibited by $Fe^{3+}$; and loses activity in the presence of $Hg^{2+}$ or $Ag^{2+}$; and
(10) Molecular Weight: About 95,500 (measured by SDS electrophoresis).

3 Claims, 3 Drawing Sheets

NOVEL α-1,6-GLUCOSIDASE AND PROCESS FOR PRODUCING THE SAME

BACKGROUND OF THE INVENTION

1. Field of the Invention

The present invention relates to a novel α-1,6-glucosidase and a process for producing the same, and more particularly to a novel α-1,6-glucosidase obtained from the culture of a novel strain of *Bacillus sectorramus* producing an α-1,6-glucosidase having an optimum pH in the vicinity of 5.0 to 5.5 and an optimum temperature in the vicinity of 55° C., and a process for producing said novel α-1,6-glucosidase which comprises collecting a-1,6'-glucosidase from the culture of said strain.

α-1,6-glucosidase is an enzyme capable of acting on an α-1,6-glucoside bond in starch or the like to produce straight chain amylose, and is widely employed in the saccharification industry for the production of maltose, glucose, and high fructose corn syrup (HFCS).

2. Related Background Art

α-1,6-glucosidase has long been found in the higher plants and yeast of microorganisms, and has recently reported to be produced by various bacteria, such as those of *Aerobactor aerogenes, Escherichia intermedia, Pseudomonas amyloderamosa, Streptococcus mites,* Cytophaga, Streptomyces, and Flavochromogenes.

On the other hand, among α-1,6-glucosidases produced by the Bacillus strains, there are already known those of *Bacillus cereus* (IFO 300), *Bacillus fermus* (IFO 3330), *Bacillus acidopullulyticus* etc.

Most of the known α-1,6-glucosidases have neutral or weakly alkaline optimum pH values and are not suitable for use in the saccharification industry, where the saccharification is conducted in acidic conditions.

As α-1,6-glucosidases having an acidic optimum pH are known to be produced by *Pseudomonas amyloderamosa* and *Bacillus acidopullulyticus*, the former is impractical for use due to poor temperature resistance, while the latter is unfavorable economically, requiring a long culture period of 60–73 hours for production.

SUMMARY OF THE INVENTION

The present inventor describes a microorganism with high productivity for an α-1,6-glucosidase having temperature resistance and an acidic optimum pH.

The present invention is based on a finding that a new Bacillus strain, newly found in soil by the present inventors, can produce a large amount of α-1,6-glucosidase in the culture within a very short culture period of 10–15 hours, which can then be collected.

According to one aspect of the present invention, there is provided a novel α-1,6-glucosidase having the following enzymochemical properties:

(1) Action: The enzyme acts on an α-1,6-glucoside bond to produce linear amylose;

(2) Substrate specificity: The enzyme has the following relative activity to selected polysaccharides:

| Polysaccharide | Relative activity (%) |
|---|---|
| Pullulan | 100 |
| Maize soluble amylopectin | 13.5 |
| Soluble starch | 6.7 |
| Oyster glycogen | 1.7 |
| Hare glycogen | 2.6 |
| Maize amylopectin | 3.8 |
| Potato amylopectin | 4.0 |

(3) Km value and Vmax to pullulan: The enzyme has a Km value of 0.14 mg/ml and a Vmax of 70.0 μmol/min/mg protein;

(4) Optimum pH: 5.0 to 5.5;

(5) pH stability: The enzyme was stable in the pH range of 4.5 to 6.5 for 30 minutes at 40° C. and in the pH range of 5.0 to 6.0 for 30 minutes at 50° C.;

(6) Optimum temperature: Approximately 55° C.;

(7) Thermal stability: Treatment at pH 4.5 for 30 minutes at different temperatures indicates that the enzyme retained 80% of the initial activity at 40° C. and 10% thereof at 60° C.;

(8) Influence of inhibitor: The enzyme is inhibited by at least 70% by p-chloromercuribenzoic acid or sodium dodecylsulfate, but is not inhibited by O-phenanthroline or potassium ferricyanide;

(9) Influence of metal salts: The enzyme is negligibly affected by $Ni^{2+}$, $Ba^{2+}$, $Zn^{2+}$, $Cd^{2+}$ or $Mn^{2+}$; is inhibited by $Fe^{3+}$; and losses activity in the presence of $Hg^{2+}$ or $Ag^{2+}$; and

(10) Molecular weight: About 95,500 (measured by SDS electrophoresis).

According to another aspect of the present invention, there is provided a process for producing α-1,6-glucosidase which comprises culturing a strain of *Bacillus sectorramus* producing α-1,6-glucosidase to produce α-1,6-glucosidase in a nutrient medium, accumulating said α-1,6-glucosidase and recovering said α-1,6-glucosidase.

BRIEF EXPLANATION OF THE DRAWINGS

FIGS. 1 to 5 show enzymochemical properties of α-1,6-glucosidase according to the present invention, wherein FIG. 1 is a graph showing an optimum pH range, FIG. 2 is a graph showing a stable pH range at 40° C. (o) and 50° C. (●), FIG. 3 is a graph showing an optimum temperature, FIG. 4 is a graph showing thermal stability, and FIG. 5 is a graph showing enzymatic stabilities at 55° C. (o), 60° C. (□) and 65° C. (●) and at various pH.

DETAILED DESCRIPTION OF PREFERRED EMBODIMENTS

Figure 1:
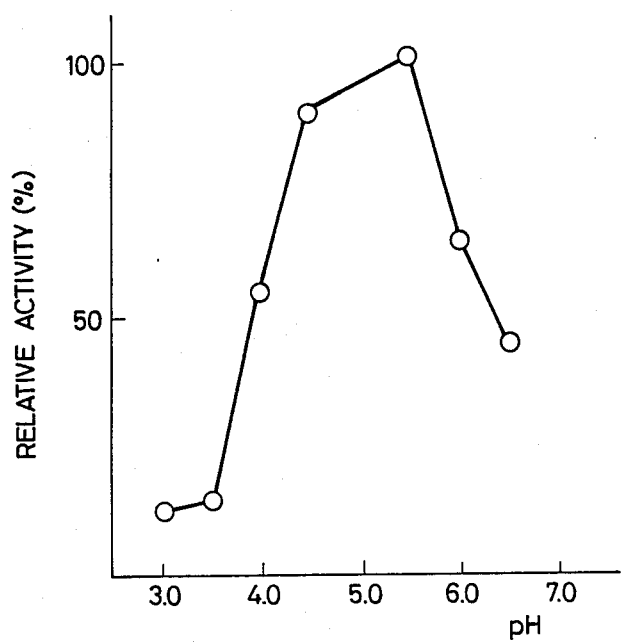

The α-1,6-glucosidase-producing strain employed in the present invention is a novel strain, which has been named *Bacillus sectorramus* by the present inventors. The strain has been deposited as FERM BP-1471 (Original Accession Number: FERM P-8973 deposited on Sept. 22, 1986) in Fermentation Research Institute, Agency of Industrial Science and Technology, of 1-3, Higashi 1-chome, Yatabe-machi, Tsukuba-gun, Ibaraki 305, Japan on Sept. 4, 1987, in conformity with Budapest Treaty on the International Recognition of the Deposit of Microorganisms for the Purposes of Patent Procedure, and will be hereinafter called the subject strain.

The subject strain has the following bacteriological properties:

| A. Form | |
|---|---|
| (1) Shape of the cell: | bacillus |
| (2) Size of the cell: | 1.0 — 1.3 × 1.5 — 5.2μ |

-continued

| | | |
|---|---|---|
| (3) Mobility: | none | |
| (4) Spore: | present | |
| (5) Gram stain: | positive | |
| (6) Acid-fast stain: | negative | |

B. Growth in various media
 (1) Standard agar plate culture:
   Colony is circular, with complete periphery.
   Surface is smooth and semitransparent gray-white.
 (2) Standard agar slant culture:
   Straight with flat surface, buttery, lustrous, medium growth.

| | | |
|---|---|---|
| (g) | Maltose | positive |
| (h) | Sucrose | positive |
| (i) | Lactose | negative |
| (j) | Trehalose | positive |
| (k) | D-sorbitol | negative |
| (l) | D-manitol | negative |
| (m) | Inositol | negative |
| (n) | Glycerin | positive |
| (o) | Starch | positive |
| (p) | Melibiose | positive |
| (q) | Salicin | negative |
| (r) | Ethanol | positive |

Key identification using the above properties, making reference to the Bergey's Manual of Determinative Bacteriology, 8th Edition Williams & Wilkins Co. (1974) and International Journal of Systematic Bacteriology, 1974–1986, reveals that the bacterium is grouped into the genus Bacillus because of gram-positive staining, the presence of spores, and aerophilic growth.

The subject strain is not identical to any known Bacillus strain, but is somewhat similar to *Bacillus cereus* or *Bacillus megaterium* because the cell is relatively wide (on the order of 1.0–1.3μ). However, these known strains can be distinguished from the subject strain in the following respects. *Bacillus cereus* grows in 7% common salt, and shows positive results with yolk reaction, casein decomposition, and gelatin decomposition. The subject strain cannot grow in 7% common salt and shows negative results with yolk reaction, casein decomposition, and gelatin decomposition.

*Bacillus megaterium* grows in 7% common salt, and shows positive results for casein decomposition and gelatin decomposition. The subject strain cannot grow in 7% common salt and shows negative results for casein decomposition and gelatin decomposition.

Furthermore, the subject strain can be distinguished from a new Bacillus strain, *Bacillus acidopullulyticus*, described in the Japanese Patent Laid-open No. 43994/1986, as summarized in Table 1:

TABLE 1

| | Subject strain | Bacillus acidopul-lulyticus |
|---|---|---|
| Oxygen demand | aerophobic | aerophilic |
| Common salt resistance | growth in 3.5% common salt | no growth in 3.5% common salt |
| Tyrosine decomposition | positive | negative |
| Assimilation of citrate | positive | negative |
| Acid production from mannitol | negative | positive |
| VP reaction | negative | variable |
| Casein decomposition | negative | variable |
| Acid production from arabinose and xylose | positive | variable |
| Width of cell | 1.0 – 1.3μ | 0.6 – 1.0μ |

Thus, the subject strain was identified as a new Bacillus strain, different from any known Bacillus strain and named as explained before.

The following will explain the process for producing and accumulating α-1,6-glucosidase by culture of the subject strain.

A suitable culture medium contained suitable inorganic salts; a carbon source (for example, starch, such as soluble starch, waxy starch, and potato starch, or hydrolysed starch, such as maltose and dextrin); and a nitrogen source (for example, hydrolyzed protein such as polypeptone, meat extract, yeast extract, corn steep liquor, diammonium phosphate, casein, or soybean protein), was found to provide a high pullulanase activity.

The subject strain was inoculated into the culture medium described above, adjusted to a pH of 4.0–7.0, and was cultivated for 1 to 2 days (10 to 20 hours for best results) at 20°–45° C., either standing or under aerobic conditions by shaking or agitating by aeration.

After the cultivation period, the cells were removed from the culture broth, and the supernatant fraction thus obtained was concentrated to obtain a preparation of crude pullulanase. This preparation was fractionated with ammonium sulfate, then subjected to affinity chromatography with γ-cyclodextrin-cephalose 6B (produced by coupling γ-cyclodextrin to activated Sepharose 6B (trade mark, Pharmacia Fine Chemical Co.)) and purified to a single band by electrophoresis utilizing SDS-polyacrylamide gel. The following explains the enzymochemical properties of the α-1,6-glucosidase thus purified.

1. Action: The enzyme acts on an α-1,6-glucoside bond to produce straight chain amylose.

2. Km value and Vmax to substrates: The Km value (mg/ml) and Vmax value (μmol/min/mg protein) of the enzyme to pullulan, potato amylopectin, and corn amylopectin are as shown in Table 2:

TABLE 2

| Substrates | Km | Vmax |
|---|---|---|
| Pullulan | 0.14 | 70.0 |
| Potato-amylopectin | 3.3 | 10.65 |
| Corn-amylopectin | 3.4 | 10.97 |

3. Relative activity to polysaccharides: Table 3 compares the relative activity of the enzyme on pullulan to relative activity on soluble maize amylopectin, soluble starch, oyster glycogen, hare glycogen, maize amylopectin, and potato amylopectin.

TABLE 3

| Polysaccharides | Relative activity (%) |
|---|---|
| Pullulan | 100 |
| Soluble maize amylopectin | 13.5 |
| Soluble starch | 6.7 |
| Oyster glycogen | 1.7 |
| Hare glycogen | 2.6 |
| Maize amylopectin | 3.8 |
| Potato amylopectin | 4.0 |

4. Optimum pH: An optimum pH was found to be 5.0–5.5 in a 25 mM citric acid- 50 mM disodium phosphate buffer (cf. FIG. 1).

Figure 2:
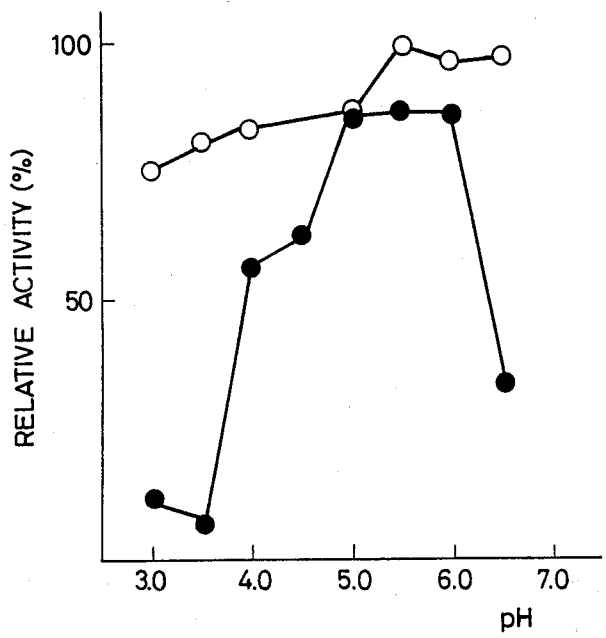

5. pH Stability: In a 25 mM citric acid - 50 mM disodium phosphate buffer, the enzyme was stable in a range of pH 4.5–6.5 after exposure to 40° C. for 30 minutes, and in a range of pH 5.0–6.0 after exposure to 50° C. for 30 minutes (cf. FIG. 2).

Figure 3:
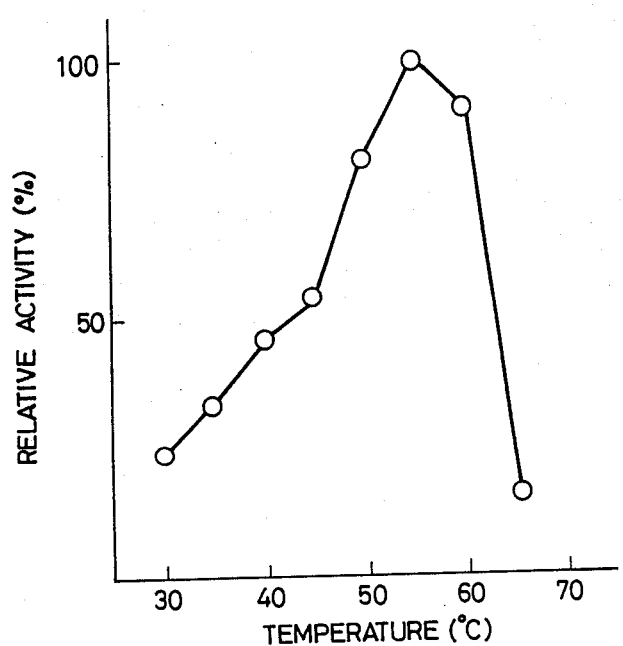

6. Optimum temperature: In a 50 mM acetic acid buffer (pH 4.5), an enzyme showed the optimum temperature of about 55° C. (cf. FIG. 3).

Figure 4:
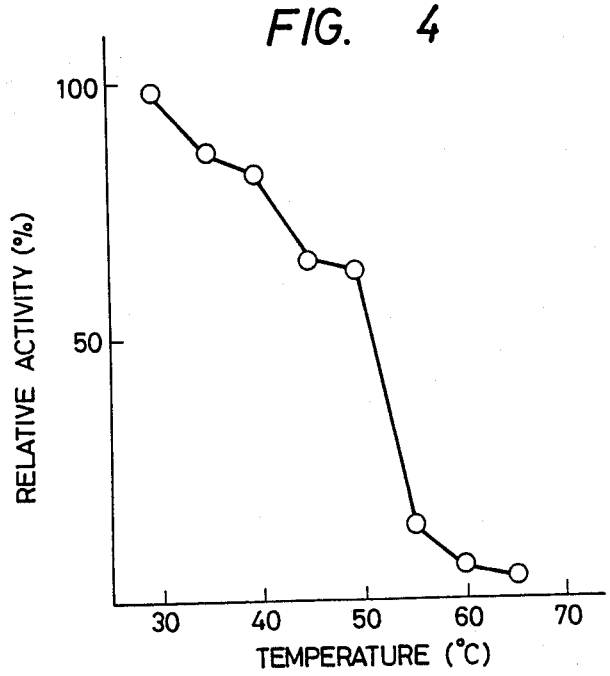

7. Thermal stability: Treatment in a 50 mM acetic acid buffer (pH 4.5) for 30 minutes at different temperatures indicated that the enzyme retained 80% of the initial activity at 40° C., but 10% thereof at 60° C. (cf. FIG. 4).

8. Assay of activity: 4 ml of 0.5% pullulan solution (pH 4.5) was added to 1 ml of an enzyme solution, and the reaction was carried out for 30 minutes at 40° C. Then, 2 ml of Somogyi solution was added, the mixture was heated for 20 minutes and then cooled. After cooling, 1 ml of ammonium arsenomolybdenate was added, and water was added to a total volume of 25 ml. Absorbance of this solution was measured at 500 nm, with a layer thickness of 1 cm. Under these conditions, the activity was defined as one unit when reducing sugar corresponding to 1 μmol of glucose was produced per minute.

9. Influence of inhibitor: The enzyme is inhibited by 70% or more by p-chloromercuribenzoic acid (PCMB) or by sodium dodecylsulfate (SDS), but not by O-phenanthroline or potassium ferricyanide. The influences of various inhibitors are shown in Table 4, indicating the remaining activity after a treatment in a 50 mM acetic acid buffer (pH 4.5) for 30 minutes at 40° C., with a final concentration of inhibitor of 1 mM.

TABLE 4

| Inhibitor | Remaining activity (%) |
|---|---|
| None | 100 |
| EDTA | 93.1 |
| o-phenanthroline | 109.0 |
| PCMB | 27.1 |
| N—ethylmaleimide | 65.5 |
| Potassium ferricyanide | 102.0 |
| SDS | 1.5 |
| Monoiodo-acetic acid | 66.5 |

10. Influence of metal salt: The enzyme is negligibly affected by $Ni^{2+}$, $Ba^{2+}$, $Zn^{2+}$, $Cd^{2+}$ and $Mn^{2+}$; is inhibited by $Fe^{3+}$; and deactivated by $Hg^{2+}$ and $Ag^{2+}$. Influences of various metal salts are shown in Table 5, indicating the remaining activity after treatment in a 50 mM acetic acid buffer (pH 4.5) for 30 minutes at 40° C., with a final concentration of metal salt of 5 mM.

TABLE 5

| Metal salt | Remaining activity (%) |
|---|---|
| None | 100 |
| $MgCl_2.6H_2O$ | 91.3 |
| $MnCl_2.4H_2O$ | 85.9 |
| $CoCl_2$ | 87.7 |
| $CaCl_2$ | 79.1 |
| $SrCl_2$ | 74.5 |
| $NiCl_2.6H_2O$ | 102.7 |
| $BaCl_2$ | 98.9 |
| $FeCl_2.nH_2O$ | 82.1 |
| $CuCl_2.2H_2O$ | 73.4 |
| $ZnCl_2$ | 97.3 |
| $HgCl_2$ | 0 |
| $AgCl_2$ | 2.7 |
| $SnCl_2.2H_2O$ | 82.1 |
| $CdCl_2.2\frac{1}{2}H_2O$ | 92.4 |
| $FeCl_3$ | 57.8 |

11. Molecular weight: ca. 95,500 (by SDS electrophoresis).

The enzyme obtained according to the present invention can be clearly distinguished, as shown in the following, from the enzyme disclosed in the Japanese Patent Laid-open No. 174,089/1982 (hereinafter called enzyme A):

1. The producing strain of the present invention is *Bacillus sectorramus*, which is a novel strain belonging to Bacillus, while that of enzyme A is the known strain *Bacillus acidopullulyticus*.

2. The optimum temperature of the enzyme produced according to the present invention is 55° C., while that of enzyme A is 60° C.

Figure 5:
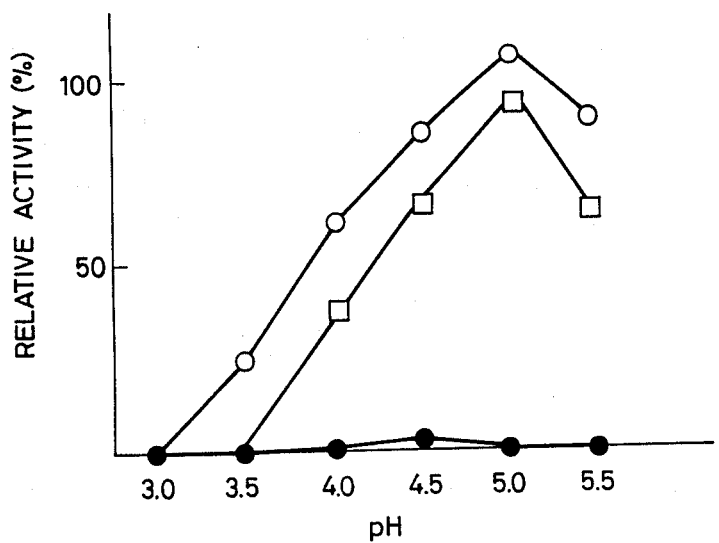

3. With regards to the enzyme activity at various pH values and temperatures, the subject enzyme shows a very large range of activity which is dependent on the temperature, as shown in FIG. 5. Also with respect to the pH dependence of the subject enzyme activity, the activity shows a peak at pH 5.0 but decreases rapidly at a higher or lower pH. Enzyme A exhibits a completely different pH and temperature profile.

4. With regards to the optimum pH, the enzyme of the present invention has a narrow optimum pH range of pH 5.0–5.5 and has a very high specificity, in contract to an optimum pH range of 3.5–5.5 for enzyme A.

Thus, the α-1,6-glucosidase obtained by the present invention can be concluded to be a novel enzyme, different from enzyme A.

The novel α-1,6-glucosidase obtained by the present invention can be added with glucoamylase in the preparation of glucose from starch, for the purpose of improving the yield, or can be used in combination with β-amylase for producing maltose from starch in high yield.

The present invention will be further explained by the following examples.

EXAMPLE 1

*Bacillus sectorramus* (FERM BP-1471) was inoculated in a medium of the following composition:

| Soluble starch | 1.5% |
| Meat extract | 0.5% |
| $(NH_4)_2HPO_4$ | 0.3% |
| $K_2HPO_4$ | 0.1% |
| $MgSO_4.7H_2O$ | 0.1% |
| Initial pH | 5.5 | and was incubated with shaking for 20 hours at 37° C. in a Sakaguchi's flask to obtain a pullulanase activity of 8.1 u/ml from the culture liquid. Cells and solids were removed from the liquid by centrifugation, and the supernatant liquid obtained was concentrated with an ultrafiltration membrane. Then, cold alcohol was added to a concentration of 80% to precipitate the enzyme, which was separated by centrifugation and lyophilized to obtain pullulanase in powder form.

EXAMPLE 2

*Bacillus sectorramus* (FERM BP-1471) was inoculated in a culture of the following composition:

| Maltose | 2% |
| Yeast extract | 0.5% |
| $K_2HPO_4$ | 0.2% |
| $MgSO_4.7H_2O$ | 0.1% |
| Initial pH | 4.5 | charged in a 30-liter jar fermenter, and cultured with stirring by aeration for 16 hours at 37° C. to obtain a pullulanase activity of 13.6 u/ml from the culture liquid. Cells and solids were removed from the liquid by centrifugation, and the supernatant liquid obtained was concentrated to ca. 1/20 with an ultrafiltration membrane, to obtain a crude liquid sample of pullulanase of 200 u/ml (pH 4.5). The sample was fractionated with ammonium sulfate and then subjected to affinity chromatography with γ-cyclodextrin-sephalose 6B to obtain a purified enzyme sample of 76.7 u/mg protein.

EXAMPLE 3

*Bacillus sectorramus* (FERM BP-1471) was inoculated in a medium of the following composition:

| Waxy starch | 2% |
|---|---|
| Polypeptone | 1% |
| $K_2HPO_4$ | 0.2% |
| $MgSO_4.7H_2O$ | 0.1% |
| Initial pH | 5.0 | charged in an 1000-liter tank, and was cultured with stirring by aeration for 15 hours at 37° C. to obtain a pullulanase activity of 18.2 u/ml from the culture liquid. The liquid was processed in a manner similar to that described in Example 2, to obtain ca. 26 liters of a crude liquid sample of pullulanase of ca. 300 u/ml.

EXPERIMENTAL EXAMPLE 1

| Substrate for saccharification: | Corn starch (33 g/dl. DE 8.0) |
|---|---|
| Enzyme for saccharification: | Gluczyme (Amano Pharmaceutical Co., Ltd.) (2.5 u/g D.S.) |
| Subject enzyme: | Liquid pullulanase obtained in Example 3 (0.1 u/g D.S.) |
| Saccharification temperature: | 62° C. |

Saccharification was conducted under the above-mentioned conditions, and the contents of monosaccharides (G1), disaccharides (G2), trisaccharides (G3), and polysaccharides (Gn) were measured by high performance liquid chromatography (HPLC) at various times. As control, measurement was made also under same saccharification conditions without using the subject enzyme, and the results are summarized in Table 6.

TABLE 6

| Reaction time | Saccharides | Enzyme added | Control |
|---|---|---|---|
| 24 hrs. | G1 | 92.6% | 90.9% |
| | G2 | 2.4% | 2.3% |
| | G3 | 0.6% | 0.4% |
| | Gn | 4.4% | 6.4% |
| 48 hrs. | G1 | 95.3% | 94.2% |
| | G2 | 2.7% | 0.3% |
| | G3 | 0.6% | 0.3% |
| | Gn | 1.4% | 2.9% |
| 72 hrs. | G1 | 95.3% | 94.7% |

TABLE 6-continued

| Reaction time | Saccharides | Enzyme added | Control |
|---|---|---|---|
| | G2 | 3.2% | 3.1% |
| | G3 | 0.6% | 0.4% |
| | Gn | 0.9% | 1.8% |

The present invention enables production of the novel α-1,6-glucosidase by the culture of a new strain *Bacillus sectorramus* (FERM BP-1471) in a short time thereby realizing economical production of thermostable α-1,6-glucosidase in a large amount and contributing to the starch saccharification industry.

We claim:

1. A novel α-1,6-glucosidase having the following properties:
   (1) Action: The enzyme acts on an α-1,6-glucoside bond to produce linear amylose;
   (2) Substrate specificity: The enzyme has the following relative activity to polysaccharides:

| Polysaccharide | Relative activity (%) |
|---|---|
| Pullulan | 100 |
| Maize soluble amylopectin | 13.5 |
| Soluble starch | 6.7 |
| Oyster glycogen | 1.7 |
| Hare glycogen | 2.6 |
| Maize amylopectin | 3.8 |
| Potato amylopectin | 4.0 |

(3) Km value and Vmax to pullulan: The enzyme has Km value of 0.14 mg/ml and Vmax of 70.0 μmol/min/mg protein;
   (4) Optimum pH: 5.0 to 5.5;
   (5) pH stability: The enzyme is stable in the pH range of 4.5 to 6.5 for 30 minutes at 40° C. and in the pH range of 5.0 to 6.0 for 30 minutes at 50° C.;
   (6) Optimum temperature: Approximately 55° C.;
   (7) Thermal stability: Treatment at pH 4.5 for 30 minutes at different temperatures indicates that the enzyme retained 80% of the initial activity at 40° C. and 10% thereof at 60° C.;
   (8) Influence of inhibitor: The enzyme is inhibited by at least 70% by p-chloromercuribenzoic acid or sodium dodecylsulfate, but is not inhibited by O-phenanthroline or potassium ferricyanide;
   (9) Influence of metal salts: The enzyme is negligibly affected by $Ni^{2+}$, $Ba^{2+}$, $Zn^{2+}$, $Cd^{2+}$ or $Mn^{2+}$; is inhibited by $Fe^{3+}$; and loses activity in the presence of $Hg^{2+}$ or $Ag^{2+}$; and
   (10) Molecular weight: About 95,500 (measured by SDS electrophoresis).

2. A process for producing an α-1,6-glucosidase comprises culturing a strain of *Bacillus sectorramus* capable of producing α-1,6-glucosidase, thereby producing α-1,6-glucosidase in a nutrient medium, accumulating said α-1,6-glucosidase and recovering said α-1,6-glucosidase.

3. The process of claim 2 wherein the strain of *Bacillus sectorramus* is strain FERM BP-1471.

* * * * *